United States Patent [19]

Capelli et al.

[11] Patent Number: 5,045,601

[45] Date of Patent: Sep. 3, 1991

[54] PRESSURE-SENSITIVE ADHESIVE COMPOSITIONS SUITABLE FOR MEDICAL USES

[75] Inventors: Christopher C. Capelli, Kenosha; Kevin Zamzow, Madison, both of Wis.

[73] Assignee: Biointerface Technologies, Inc., Madison, Wis.

[21] Appl. No.: 365,313

[22] Filed: Jun. 13, 1989

[51] Int. Cl.⁵ .............................................. C08L 75/00
[52] U.S. Cl. ............................... 525/327.1; 528/112; 528/20; 528/28; 528/49; 528/59; 528/61; 528/65; 528/66; 528/288; 424/445; 427/372.2; 428/343
[58] Field of Search ..................... 528/112, 20, 28, 49, 528/59, 61, 65, 66, 288; 525/327.1; 424/445; 427/372.2; 428/343

[56] References Cited

U.S. PATENT DOCUMENTS

| | | | |
|---|---|---|---|
| Re. 31,887 | 5/1984 | Hodgson | 428/355 |
| 3,645,835 | 2/1972 | Hodgson | 161/146 |
| 3,648,835 | 3/1972 | Yucel | 206/59 |
| 3,769,071 | 10/1973 | Trancik | 117/122 |
| 3,796,678 | 3/1974 | Bartizal | 260/29.2 |
| 3,896,789 | 7/1975 | Trancik | 128/2 |
| 4,156,066 | 5/1979 | Gould | 528/73 |
| 4,156,067 | 5/1979 | Gould | 528/73 |
| 4,233,969 | 11/1980 | Lock et al. | 128/156 |
| 4,307,717 | 12/1981 | Hymes et al. | 128/156 |
| 4,310,509 | 1/1982 | Berglund et al. | 424/28 |
| 4,323,557 | 4/1982 | Rosso et al. | 424/28 |
| 4,340,043 | 7/1982 | Seymour | 128/132 |
| 4,360,369 | 11/1982 | Niederer | 55/283 |
| 4,367,732 | 1/1983 | Poulsen et al. | 128/156 |
| 4,442,259 | 4/1984 | Isgur et al. | 524/839 |
| 4,460,369 | 7/1984 | Seymour | 604/897 |
| 4,507,430 | 3/1985 | Shimada et al. | 524/839 |
| 4,542,012 | 9/1985 | Dell | 424/28 |
| 4,554,317 | 11/1985 | Behar et al. | 525/28 |
| 4,614,787 | 9/1986 | Szyeher et al. | 528/75 |
| 4,626,475 | 12/1986 | Goel et al. | 428/423 |
| 4,638,797 | 1/1987 | Merrill et al. | 128/156 |
| 4,643,180 | 2/1987 | Feld et al. | 128/156 |
| 4,661,099 | 4/1987 | Bittera et al. | 604/290 |
| 4,675,009 | 6/1987 | Hymes et al. | 604/304 |

*Primary Examiner*—Maurice J. Welsh
*Attorney, Agent, or Firm*—Foley & Lardner

[57] ABSTRACT

A dermatologically-acceptable, moisture vapor-permeable, pressure-sensitive adhesive composition that is a single-phase solid at ambient temperature and resists dissolution when exposed to water, comprises a polymer adhesive which is the product of a process comprising the steps of chain extending a water-soluble derivatized capped prepolymer which comprises a first terminal group and a low-temperature curable group, until the resultant polymer attains a determined level of tackiness, and then subjecting the polymer to low-temperature curing. The adhesive is used to advantage in medical products like adhesive bandages, plasters, dressings and surgical drapes, and can dissolve water-soluble bio-active additives.

53 Claims, No Drawings

PRESSURE-SENSITIVE ADHESIVE COMPOSITIONS SUITABLE FOR MEDICAL USES

BACKGROUND OF THE INVENTION

The present invention relates to adhesive materials, and particularly to a new group of dermatologically acceptable, moisture vapor-permeable, pressure-sensitive adhesive compositions which can be used in various medical contexts, including as a component of a wound dressing.

Wound management has developed rapidly in recent years due to advances in the understanding of the wound healing process and to the advent of new materials and techniques for use in wound dressings. In particular, much activity has occurred in the development of pressure-sensitive adhesive, moisture vapor-permeable wound dressings. These wound dressings provide coverings that protect wounds from further harm, enhance the natural healing process, and prevent bacterial invasion. Despite the availability of these newly-developed materials, infection is still a common complication associated with conventional dressings.

A wound is a loss of continuity of skin or mucous membrane due to accidental injury or planned surgery. Wound healing is essentially the replacement of dead or damaged tissue by healthy, living cells. Healing can occur either by partial or complete regeneration or by repair. Regeneration implies complete restitution to regain the original tissue structure. Repair, on the other hand, involves formation of a new permanent structure, a scar. Wound healing is typically a two-step process, involving regeneration of epithelial tissue and repair of connective tissue.

Among the various factors which affect wound healing are, for example, host resistance, environment and location of the wound, and the presence of bacteria. The patient's overall health, metabolic and nutritional status determine resistance. Blood flow, lymphatic drainage, temperature and humidity are important in respect of the environment and location of a wound. Bacteria at the wound site can proliferate and cause infection.

Wound dressings should possess a number of important characteristics in order to protect the wound and enhance its ability to heal. An ideal wound dressing should (i) have optimal water permeability to prevent desiccation of the wound and fluid accumulation under the covering; (ii) prevent microbial invasion from the environment; (iii) have no antigenic properties; (iv) be an elastic-plastic film to facilitate intimate covering of all possible contours of the human body; (v) be capable of both adhering well to the wound and being readily removable without causing any damage to the tissue beneath the covering; and (vi) be inexpensive to produce and readily amenable to storage.

Modern wound dressings are generally constructed of a backing sheet with a pressure-sensitive adhesive on one side. The backing sheet is typically moisture vapor permeable, allowing water vapor to escape from the wound site while preventing liquid water from entering or escaping from the site. In addition, bacteria are prevented from passing through the wound dressing. The adhesive provides the desired pressure-sensitive adherence for securing the backing to the wound site and retaining the backing in the desired position.

High moisture vapor-permeability of a dressing prevents maceration of the skin due to occlusion of transepidermal fluid lost from the body and delamination of the dressing from the wound site, as will be explained below. Many modern wound dressings are known for their high moisture vapor-permeability, as measured by the moisture vapor transmission rate (MVTR). For example, U.S. Pat. Nos. 4,340,043 and 4,360,369 disclose an adhesive-coated, polymeric sheet material having a high MVTR. This material is commercially available as a wound dressing marketed, under the mark Op-Site ®, by Nephew & Smith, Ltd. See also U.S. Pat. No. 4,233,969.

The moisture permeability of such dressings is a function of the moisture permeability of both the polymeric film and the pressure-sensitive adhesive used. Many wound dressings use moisture permeable adhesives. For example, U.S. Pat. No. 3,645,835 (Hodgson) discloses both a moisture vapor-permeable backing material and a moisture vapor-permeable pressure-sensitive adhesive. The Hodgson patent also teaches that both the backing material and adhesive are unaffected by water, i.e., they neither swell nor absorb water. U.S. Pat. Re. No. 31,887, a reissue of the Hodgson patent, specifically discloses the backing material as a polyurethane and the adhesives as a polyvinyl ethyl esters or an acrylate. See also U.S. Pat. No. 4,638,797.

Polyurethane adhesives have been developed which are suitable for wound dressings. For example, U.S. Pat. No. 3,796,678 discloses a polyurethane adhesive which is highly branched and isocyanate-blocked with mono-functional alcohols. U.S. Pat. No. 4,626,475 relates to a polyurethane having improved adhesive properties, accomplished by using a bicyclic amide acetal additive. Aqueous-based polyurethane adhesives have also been developed. See, for example, U.S. Pat. Nos. 4,442,259 and 4,507,430. As explained above, the overall goal of wound dressings is to prevent infection and to provide an environment that promotes wound healing. To prevent infections, modern wound dressings are continuous, or occlusive, that is, there are no openings in the dressing through which bacteria from the environment can reach the wound site. Even with an occlusive dressing, however, infection may occur at the wound site if the dressing loses its integrity or if bacteria are already present at the wound site or the surrounding skin. Loss of integrity allows microbes from the environment to reach the wound site and cause infection. Bacteria already present at a wound site can also proliferate and cause infection.

The principle cause of integrity failure of an occlusive film dressing is delamination of the dressing from the wound site. Delamination is a function of the moisture permeability of the dressing and the ability of the dressing to absorb fluid. If the dressing does not have a high enough MVTR, then fluid from the wound or surrounding skin can accumulate. If the pressure-sensitive adhesive used neither absorbs this fluid nor allows it to reach an absorbent layer, then delamination between the pressure-sensitive adhesive and the wound site and/or surrounding skin will occur. If the delamination reaches the edge of the dressing, loss of dressing integrity results in the wound site being exposed to environmental microbes, i.e., loss of the bacterial barrier. The integrity of a dressing thus, is a function of both its moisture vapor permeability and fluid swellability. One of the major problems with current wound dressings is the use of materials with an insufficiently high MVTR to avoid delamination and pressure-sensitive adhesives unable to absorb fluid.

Attempts have been made to develop water-swellable adhesives by incorporating various substances into the adhesive which absorb water. Most of these attempts utilize gel adhesives. For example, U.S. Pat. No. 4,661,099 discloses a water-absorptive polyurethane gel adhesive wherein polyols are immobilized in the cross-linked polyurethane. U.S. Pat. No. 4,367,732 relates to a polystyrene-based gel adhesive in which water-swellable hydrocolloids are dispersed. See also U.S. Pat. No. 3,648,835 and Re. No. 31,887. Upon absorbing water, such gels tend themselves to dissolve in the water. Gel adhesives generally lack the inherent stability and storage convenience of solid adhesives. See also U.S. Pat. Nos. 4,233,969, 4,156,066 and 4,156,067, directed to polyurethane films that are water-swellable.

Even if a dressing maintains integrity, the enclosed environment provided by dressings may allow bacteria present at the wound site on the surrounding skin to multiply unduly and lead to infection. Numerous bacteria are present on human skin. Some may survive an initial application of a topical antimicrobial agent and act as seeds for subsequent growth. Continuous application of an antimicrobial agent would be highly desirable.

Recently, several wound dressings have been developed wherein an antimicrobial agent is applied or added to the polymeric film or, more preferably, to the adhesive. For example, U.S. Pat. Nos. 4,554,317 and 4,643,180 disclose application of an agent to the surface of a membrane or adhesive, respectively. Other attempts have been directed to the formation of a chemical complex between the antimicrobial agent and the film or adhesive. U.S. Pat. Nos. 4,542,012 and 4,323,557 teach complexing iodine with polyvinylpyrrolidone residues in polymer. Release of the antimicrobial agent depends, however, on its appropriate dissociation from the chemical complex.

Still other prior art dressings teach a physical combination of the antimicrobial agent and polymer or adhesive. For example, U.S. Pat. No. 4,614,787 discloses a pharmacologically active agent dispersed through a cured polymeric film to which an adhesive may be applied. U.S. Pat. No. 4,310,509 discloses a flexible-backing material to which is applied a composition of a broad-spectrum antimicrobial agent homogeneously and stably dispersed in a pressure-sensitive adhesive. U.S. Pat. No. 4,460,369 discloses an adhesive-coated, liquid-impervious, moisture vapor-permeable, thin polymer sheet in which a solid antibacterial material in a finely divided form is incorporated within the adhesive. U.S. Pat. Nos. 4,156,066 and 4,156,067 disclose that a medicament may be added to a lactone-modified polyurethane which is applied to the skin as a film. See also U.S. Pat. Nos. 3,896,789 and 3,769,071, which disclose addition of other bioactive agents, such as retinoic acid and 5-fluorouracil, to a polyurethane adhesive.

A problem inherent in these prior art attempts is that since most adhesives are not water-soluble, water-soluble antimicrobials may only exist as a separate phase dispersed throughout the adhesive. For example, the Berglund Pat. discloses that if an antimicrobial is water-soluble and is in a water solution, a stable water-in-oil emulsion is formed upon mixing with the adhesive. If, on the other hand, an antimicrobial is soluble in an organic solvent and is in solution in that solvent, and the organic solvent is miscible with the adhesive solution, then the solvent of the adhesive extracts the solvent of the antimicrobial solution, causing the antimicrobial to separate out as distinct, minute, separate phase particles.

Still another approach utilizes adhesives in which the bioactive agent can be truly dissolved in the adhesive. For example, U.S. Pat. Nos. 4,307,717 and 4,675,009, both issued to Hymes et al., disclose a flexible backing material provided with a hydrophilic, adhesive matrix which has a solid phase of a polysaccharide and a liquid phase of an alcohol, carbohydrate and/or protein, where a medicinal agent is "molecularly dispersed," rather than encapsulated, in the matrix. The Hymes '009 Pat. is a continuation-in-part of the '717 Pat. and states that the adhesive is capable of absorbing moisture and that the medicinal agent is "molecularly dissolved and/or suspended" in the adhesive matrix.

Despite recognition of the many practical wound dressing design problems, proper solution to all these problems in a single wound dressing has not been demonstrated in the prior art. Despite improvements in modern wound dressings, dressing materials are needed that comprise higher-MVTR compositions and pressure-sensitive adhesives. The MVTR of a pressure-sensitive adhesive is usually the limiting factor in the total moisture permeability of a film-backed dressing. Moreover, even though adhesives should optimally absorb or transport fluid, nearly all medically suitable, pressure-sensitive adhesives which are currently available are unaffected by water, i.e, they neither swell nor absorb water.

While effective to some degree, conventional wound dressings which incorporate drugs and other bioactive agents in a pressure-sensitive adhesive layer are generally limited to solvent-based (rather than aqueous-based) antimicrobial agents or drugs, since most pressure-sensitive adhesives are hydrophobic. When water-soluble agents are placed within these adhesive systems, water-in-oil emulsions form or the agents precipitate out as solid particles. Release of the agent requires diffusion of particulates through a hydrophobic matrix.

SUMMARY OF THE INVENTION

It is therefore an object of the present invention to provide a film-backed adhesive material which includes a pressure-sensitive polyurethane adhesive characterized by a unique balance of both hydrophilic and hydrophobic characteristics, such as moisture vapor-permeability, an ability to absorb fluid without dissolving, and a capability to dissolve water-soluble agents in a solid solution, rather than forming an emulsion or precipitate.

It is also an object of the present invention to provide a medically suitable, pressure-sensitive adhesive that has a very high moisture vapor-permeability and, thus, minimizes fluid accumulation due to trapped moisture beneath the adhesive.

It is additionally an object of the present invention to provide a pressure-sensitive adhesive that swells without dissolving on exposure to water or other body fluids and, thus, minimizes delamination between the wound site and adhesive due to fluid accumulation.

It is a further object of the present invention to provide a pressure-sensitive adhesive within which water-soluble bioactive agents may be dissolved.

It is yet another object of the present invention to provide a method for the ready preparation of a wound dressing, which method can accommodate the use of water-soluble, bioactive agents without the disadvantages of precipitation and emulsion-formation discussed above.

In accomplishing the foregoing objects, there has been provided, according to one aspect of the present invention, an adhesive composition which comprises a polymer adhesive that is soluble or dispersible in water and is low-temperature curable to form a solid which is single-phase at ambient temperature, pressure-sensitive, dermatologically acceptable, moisture vapor-permeable and resistant to dissolution when exposed to water. The adhesive composition preferably contains a bioactive agent dissolved therein.

In a preferred embodiment, the polymer adhesive is the product of a process comprising the steps of (A) reacting a prepolymer compound comprising a plurality of hydroxyl groups and a polyisocyanate capping agent to form an isocyanate-terminated capped prepolymer comprising polyurethane units; (B) reacting a portion of the terminal isocyanate groups of the capped prepolymer with a derivatizing agent comprising a group reactive with isocyanate, in particular a hydroxyl group, and a low-temperature curable group to form a derivatized capped prepolymer; and (C) reacting the derivatized capped prepolymer with a chain extension agent reactive with isocyanate, in particular with water, to effect chain extension of the derivatized capped prepolymer, whereby a polymer is formed, until the polymer attains a determined level of tackiness, at which point chain extension is halted by addition of a chain termination agent reactive with isocyanate.

In accordance with another aspect of the present invention, there is provided a cured adhesive composition comprising a polymer adhesive which is the product of a process comprising the steps of (A) providing a water-soluble derivatized capped prepolymer, (B) subjecting the derivatized capped prepolymer to chain extension to form a polymer, until a determined level of tackiness is attained, wherein a chain termination agent is added, and (C) subjecting the polymer to low-temperature curing. Preferably, a bioactive agent is dissolved in the adhesive.

In accordance with yet another aspect of the present invention, there is provided a water vapor-permeable, pressure-sensitive adhesive wound dressing, comprising a flexible backing coated with a pressure-sensitive adhesive layer provided on at least a portion of the surface of the backing, wherein the adhesive layer comprises a cured adhesive composition as described above, preferably comprising a bioactive agent dissolved therein.

In accordance with a further aspect of the present invention, there is provided a process for producing a wound dressing as described above.

In accordance with yet a further aspect of the present invention, there is provided a process for producing an uncured polymer adhesive as described above.

In accordance with still another aspect of the present invention, there is provided a process for producing a cured polymer adhesive as described above.

Other objects, features and advantages of the present invention will become obvious to those skilled in the art from the following detailed description. It should be noted, however, that the detailed description and specific examples, while indicating preferred embodiments of the present invention, are given by way of illustration and not limitation. Many changes and modifications may be made within the scope of the present invention without departing from the spirit thereof, and the invention includes all such changes.

DETAILED DESCRIPTION OF PREFERRED EMBODIMENTS

In the following description of the present invention, process steps are carried out at room temperature and atmospheric pressure unless otherwise specified. The phrase "pressure-sensitive adhesive" means that a composition thus qualified is inherently tacky, viscoelastic and cohesive in its dry (cured) state. The expression "aqueous-based" refers to a solvent or carrier which is water or a mixture of water and a miscible solvent such as an alcohol. The term "low-temperature curable" refers to groups which are capable of cross-linking under the influence of actinic radiation, which includes ultraviolet light and electron emission, as well as free radicals, pH shift or other mechanisms which are capable of functioning at approximately room temperature. The term "polyfunctional" is used with reference to a compound having two or more reactive groups, including low-temperature curable groups. A material is "dermatologically acceptable" if it does not cause noticeable skin irritation.

Polymer adhesives according to the present invention are preferably obtained by treating a water-soluble compound, referred to as a derivatized capped prepolymer, which comprises a plurality of first terminal groups and a plurality of low-temperature curable groups, with a second compound, referred to as a chain extension agent, which is reactive with the first terminal groups, resulting in formation of a polymer. The chain extension is terminated when the resulting polymer achieves a desired tackiness, by reacting the polymer with a third compound, referred to as a chain termination agent, reactive with the first terminal group. Incorporation of the chain termination agent into the chain halts further chain growth and completes formation of the uncured polymer adhesive. Preferably the derivatized capped prepolymer is reacted with an excess of the chain extension agent, based on the content of the first terminal group of the derivatized capped prepolymer.

Preferably the first terminal group is an isocyanate group, in which case the chain extension agent is preferably water, a polyol or a polyamine. The first terminal group may also be an ester group, in which case the chain extension agent is preferably ammonia or a polyamine. The first terminal group may also be an isothiocyanate group.

The chain extension is preferably conducted using at least a two-fold equivalent excess of the chain extension agent.

The chain extension reaction may be conducted at room temperature or at elevated temperatures of up to approximately 100° C. In general, temperatures of about 20° C to about 90° C. can be used to increase the reaction rate. Elevated temperature may be particularly advantageous where the derivatized capped prepolymer has been prepared using an aliphatic polyisocyanate.

The chain extension reaction is allowed to proceed until the reaction mixture acquires a desired adhesive capability. The characteristics of the adhesive or adhesive capability are generally given in terms of optimal bonding strength for a given substrate or substrates at workable viscosity levels. Adhesive capability of the reaction mixture can be tested qualitatively or quantitatively. Qualitative monitoring simply involves removing samples from the reaction mixture and evaluating their adhesive properties by touch or by an elementary test of adhesiveness between two substrates. In more quantitative procedures, the reaction mixture is monitored, for example, via measurement of viscosity.

In general, the viscosity of the reaction mixture increases as the chain extension reaction proceeds. Sufficient correlation may be established between the viscosity of the reaction mixture and its adhesive capability to permit the use of viscosity measurements as a means of monitoring the reaction. Useful viscosities may vary over a wide range, depending on such factors as the nature of the derivatized capped prepolymer, the percent solids of the reaction mixture, and the temperature of the reaction mixture.

A chain termination agent may be added to control the chain extension of the derivatized capped prepolymer, that is, to slow the reaction and prevent gelation of the derivatized capped prepolymer, before complete termination of the polymerization. The amount of chain termination agent used depends on such factors as the comparative reactivities of the chain extension agent and the chain termination agent with the derivatized capped prepolymer, and the desired rate of reaction. The monofunctional chain termination agent used to control chain extension of the derivatized capped prepolymer may be any compound capable of reacting with the first terminal group so as to retard or prevent its reaction with the chain extension agent. A variety of monofunctional chain termination agents are suitable. Where the first terminal group is an isocyanate group, suitable monofunctional chain termination agents include alcohols, such as methanol, ethanol, isopropanol and phenol; primary or secondary monamines like ammonia, methylamine, ethylamine and isopropylamine; oximes such as acetone oxime, butanone oxime, cyclohexanone oxime; and alkanol amines like ethanol amine. In accordance with another aspect of the present method, a combination of two or more monofunctional chain termination agents can be used. An example of such a combination, used where the first terminal group is an isocyanate group, is that of an alcohol with a more reactive chain termination agent, such as an oxime. The alcohol in the combination may provide some chain termination function but is used primarily as a diluent or co-solvent, while the more reactive chain termination agent provides the major proportion of the reaction with the isocyanate group.

In addition to alcohols, other co-solvents may be employed pursuant to the present invention. These co-solvents should be miscible with water or a water-alcohol mixture and, unless intended for use as a monofunctional chain termination agent, should be inert to the first terminal groups. Preferred co-solvents are volatile solvents, such as acetone or methyl ethyl ketone, the use of which can facilitate drying of the adhesive compositions. The co-solvent may be added prior, during, or subsequent to chain extension.

When the desired viscosity and/or adhesive capability has been attained, additional monofunctional chain termination agent, e.g., the chain termination agent used for reaction control or a second, different agent reactive with the first terminal group, is added to the reaction mixture in an amount at least equal to or substantially greater than the amount of unreacted first terminal groups in the derivatized capped prepolymer, on an equivalent basis. The amount of unreacted first terminal groups remaining in the derivatized capped prepolymer at the time the desired adhesive capability is attained will vary with the nature of the derivatized capped prepolymer and the degree of chain extension. Although this amount can be measured, thereby allowing calculation of the minimum quantity of additional chain termination agent to be added, it is generally more convenient and satisfactory to simply employ an excess amount of the chain termination agent.

By reaction of the additional chain termination agent with the remaining first terminal groups in the derivatized capped prepolymer, the chain extension reaction is terminated. The effectiveness of the chain termination agent in terminating chain extension, i.e., the rate and extent of reaction with the remaining first terminal groups is increased by using an excess amount of the agent and, consistent with such increased effectiveness, the resultant adhesive compositions tend to have a longer shelf life. Reasonable excesses of the additional chain termination agent, for example, in the range of a 10% to 100% equivalent excess, in general do not adversely effect the adhesive capability.

The additional chain termination agent should be capable of forming a reaction product with the first terminal group that is very stable to water, for reasonable periods of time at room temperature. The additional chain termination agent can be any of the aforementioned monofunctional chain termination agents, or may be a polyfunctional chain termination agent such as a diol, diamine or dioxime. Preferred chain termination agents are the more reactive monofunctional materials, exemplified by the aforementioned oximes and amines. It is also possible to use ammonia. Although alcohols can be used as the additional chain termination agent, and are often added in excess for such purpose and for purposes of dilution, they are preferably employed in conjunction with a more reactive chain termination agent to insure a maximum shelf life for the product. For example, various primary and secondary amines may be used in conjunction with the alcohol; ammonia is particularly useful in this regard.

The additional chain termination agent may be added to the reaction mixture at any temperature up to about 100° C. Generally, the same temperature used for chain extension is also used for this addition.

The derivatized capped prepolymer is preferably formed by reacting a second water-soluble compound, referred to as a capped prepolymer, which comprises a plurality of the first terminal groups, with a derivatizing agent. The derivatizing agent comprises a first functional group which is reactive with the first terminal groups, and a second functional group which is low-temperature curable. The reaction is carried out such that a portion of the first terminal groups of the capped prepolymer are reacted with the first functional groups of the derivatizing agent, leaving the remainder of the first terminal groups available to react with the chain extension agent to effect polymerization.

The second functional group, i.e. the low-temperature curable group, preferably is curable under the action of actinic radiation, which includes ultraviolet radiation and electron emission, as well as pH shift or free radicals. In a preferred embodiment, the low-temperature curable group is an ethylenically unsaturated group, and particularly preferably is an activated vinyl group.

Preferably, about 5 to 80% of the first terminal groups of the capped prepolymer are reacted with the first functional group of the derivatizing agent. Particularly preferably, 5 to 50% of said first functional groups are so reacted.

In a preferred embodiment, the first terminal group of the capped prepolymer is an isocyanate group and the first functional group of the derivatizing agent is a hydroxyl or amine group. The derivatizing agent is preferably a hydroxyalkyl ester of a $(C_1-C_6)$-$\alpha,\beta$-unsaturated carboxylic acid. Suitable esters include hydroxyalkyl acrylates, methacrylates, crotonates and itaconates. The hydroxyalkyl ester is preferably a hydroxyethyl ester, such as hydroxyethyl acrylate and hydroxyethyl methacrylate. Other examples of suitable acrylates include 1,2,6-hexanetriol diacrylate, pentaerythritol triacrylate and neopentaerythritol triacrylate.

The first terminal group may also be an ester group, in which case the first functional group is preferably an amine group. In this embodiment, the derivatizing agent is preferably an aminoalkyl amide of a $(C_1-C_6)$-$\alpha,\beta$-unsaturated carboxylic acid. Suitable amides include aminoalkyl acrylamides, methacrylamides, crotonamides and itaconamides.

The capped prepolymer is preferably formed by reacting a polyfunctional compound, hereinafter referred to as a capping agent, which comprises a plurality of the first terminal group with a water-soluble prepolymer which comprises a plurality of a second terminal group reactive with the first terminal group. The capping agent reacts with the terminal groups of the prepolymer, and thus "caps" the prepolymer with first terminal groups on the terminal ends of the prepolymer.

In a preferred embodiment, the first terminal group is an isocyanate group and the second terminal group is a hydroxyl group. This results in formation of a urethane capped prepolymer. These prepolymers are prepared by the well-known method of reacting a polyol with an aliphatic or aromatic polyisocyanate. Particularly preferably, the prepolymer is a polyoxyalkylene polyol or a polyester polyol. Carboxymethylcellulose can also be used as the prepolymer. Excess polyisocyanate is usually employed to insure reaction of all the polyol hydroxyl groups and to minimize crosslinking due to reaction of two or more isocyanate groups of the same molecule.

Particularly preferred polyols used in accordance with the present invention are hydrophilic polyoxyethylene polyols, that is, hydrophilic polyols comprising recurring oxyethylene ($-CH_2-CH_2-O-$) units. These polyols and the prepolymers prepared from them exhibit an especially high degree of hydrophilicity, particularly those comprising at least 20 mole %, more particularly at least 40 mole % oxyethylene units. Such polyols and prepolymers are therefore especially suitable, in terms of water solubility and reactivity, for use in accordance with the present invention.

The advantages attendant to the hydrophilicity of the polyoxyethylene polyols also extend to the adhesive materials in accordance with the invention. Adhesive compositions can be prepared to have a relatively high solids content, for example, as high as 60% on a weight basis, and have favorable stability characteristics, i.e., minimal or no tendency to form gels or to coagulate while sitting or to undergo phase separation. Also, the compositions can be readily diluted with polar solvents such as water and alcohols.

The advantages realized by the use of hydrophilic polyoxyethylene polyols and prepolymers are obtained without the use of surfactants, thus avoiding the presence of such materials and their effects on process steps of the present invention. Such surfactants are commonly necessary for reactions of more hydrophobic prepolymers.

The use of excess capping agent, such as polyisocyanate, in preparing the capped prepolymers will generally provide a composition containing unreacted capping agents. Chain extension of the resulting derivatized capped prepolymer thus entails reaction of the first terminal groups of such unreacted capping agents.

Although polyisocyanates having an isocyanate functionality of three or more may be used in preparation of prepolymers used herein, it is generally preferred to employ diisocyanates. Both aliphatic and aromatic diisocyanates can be used. Suitable diisocyanates include: 1,6-hexamethylene diisocyanate, isophorone diisocyanate, 2,3,4-trimethyl-1,6-hexane diisocyanate, trimethylene di isocyanate, toluene-2,4-diisocyanate, diphenylmethane-4,4'-diisocyanate, biphenyl-4,4'-diisocyanate, and 3,3'-dimethyl-4,4'-diisocyanate-1,1'-biphenyl.

Aliphatic polyisocyanates are preferred insofar as the resultant prepolymers generally react more slowly with water than those prepared from aromatic polyisocyanates. This permits better process control, and possibly the use of less monofunctional chain termination agent. However, from the standpoint of minimizing reaction time, prepolymers prepared from aromatic polyisocyanates are preferred albeit in the presence of a potentially greater amount of chain termination agent. Other considerations which might effect the choice of a particular polyisocyanate include the hydrophobic/hydrophilic properties imparted to the resultant prepolymer and factors such as cost, availability and toxicity.

In another preferred embodiment, the first terminal group is an ester group and the second terminal group is an amine group. In this embodiment, the prepolymer is preferably a polyaminoalkylene polyamine.

The prepolymer is preferably formed by reacting a first water-soluble monomer which comprises a plurality of the second terminal group with a second water-soluble monomer which is reactive with the second terminal group. When the second terminal group is a hydroxyl group, the first water-soluble monomer is preferably a polyol and the second water-soluble monomer is preferably an epoxide compound such as ethylene oxide or propylene oxide; these monomers react to form the preferred polyoxyalkylene polyols. Suitable polyols include ethylene glycol, glycerol, trimethylolpropane and pentaerythritol, and also a mixture of ethylene glycol and glycerol. The prepolymer preferably has a molecular weight of about 3 to 15 kilodaltons. The resulting isocyanate capped prepolymer has an NCO-value of 2.5–3.0, that is, the average capped prepolymer comprises 2.5–3.0 unreacted isocyanate groups.

The preferred polyoxyethylene polyols may comprise only recurring oxyethylene units, or may comprise other recurring units provided by other alkylene oxides. Where the polyols comprise more than one type of oxyalkylene units, the recurring oxyethylene units should be present in sufficient amount to provide a satisfactory hydrophilic/hydrophobic balance and, as indicated above, an oxyethylene content of at least 20 mole %, more particularly at least 40 mole %, is preferred. The polyoxyethylene polyols can be admixed with other polyols, including hydrophobic polyols, prior to reaction with the polyisocyanate, again provided that a satisfactory hydrophilic/hydrophobic balance is provided.

When the second terminal group is an amine group, the first water-soluble monomer is preferably a polyamine and the second water-soluble monomer is preferably an aziridene compound. Particularly preferably, the first water-soluble monomer is ethylenediamine and the second water-soluble monomer is aziridene.

In another preferred embodiment, the prepolymer is a copolymer. In this embodiment, the prepolymer preferably comprises polyvinylpyrrolidone.

Alternatively, the derivatized capped prepolymer may be formed directly by reacting a water-soluble prepolymer with one or more siloxane compounds comprising a low-temperature curable group.

After the derivatized capped prepolymer has been chain-extended and the remaining first terminal groups have been reacted with a chain termination agent, a photoinitiator may be added to the reaction mixture, in an amount from about 0.1% to 5% by weight of the reaction composition. Suitable photoinitiators include benzophenone, acetophenone, azobenzene, acenaphthenequinone, o-methoxybenzophenone, thioxanthen-9-one, xanthen-9-one, 7-H-benz(de)anthracen-7-one, 1-naphthaldehyde 4,4'-bis(dimethylamino)- benzophenone, fluorene-9-one, 1'-acetonaphthone, 2'-acetonaphthone, anthraquinone, 2-tert-butyl anthraquinone, 4-aminobenzophenone, 4'-methoxyacetophenone, 2,2-diethoxyacetophenone, and benzaldehyde.

The adhesive composition of the present invention is aqueous-based, that is, the adhesive carrier or solvent includes water in large quantity, including residuum from the preparatory reaction and any amount added thereafter. In general, the carrier comprises at least 10% water by weight, with a proportion of up to 75% by water typically acceptable. An adhesive composition according to the present invention can be used as is or, if desired, can be diluted with water, an alcohol, or another water-miscible solvent. The solutions tend to be infinitely dilutable with alcohols and with water/alcohol mixtures containing about 50% or more by volume of alcohol. They may also be diluted with water alone to a solid content of about 15% to 20% on a weight basis. As a function of the particular adhesive prepared, and of the presence of co-solvents in the composition, the polymeric adhesive may begin to precipitate below about 15% water content.

A major advantage of an adhesive composition within the present invention is an ability to be diluted with water and, hence, the ability to dissolve water-based agents and drugs to form a solid solution, without the agent or drug precipitating or forming an emulsion. A large variety of water-based drugs, including heat labile drugs, may be dissolved in the compositions of the present invention due to its water miscibility and low temperature of curing, as is explained below. It is contemplated that any coagulant, antibiotic, antifungal agent, topical anesthetic, anti-inflammatory agent or mixture thereof that is water soluble or water miscible may be dissolved in the adhesive composition. Examples of such agents include an enzyme, a protein, a growth factor, a hormone, a biocidal agent, an antiseptic agent, an antibacterial agent, an antifungal agent, an antiviral agent, an anti-histamine, an anti-inflammatory agent, an anti-pruritic agent, a keratolytic agent, an skin-protective agent, a rubefacient, a topical anesthetic, a hemostatic agent, an anti-anginal agent, a vitamin, a nutritional mineral, a water-soluble polyol compound, collagen or nicotine. In particular, enzymes, such as papain, trypsin, collagenase, subtilisin, ficin, pepsin, lysozyme, streptokinase, fibrinolysin, pinguinain, travase, bromelin and glucose oxidase; antibiotics such as gentamicin sulfate; anti-microbials like polyvinylpyrrolidone-iodine and chlorhexidine digluconate; growth factors, including platelet-derived growth factor, transforming growth factors-$\alpha$ and -$\beta$, fibroblast growth factor, epidermal growth factors and angiogenesis factor; thrombin and other hemostatic agents; water-soluble cellulose compounds, including alkali metal salts of carboxymethyl cellulose, hydroxyethyl cellulose; polyols including polyoxyethylene, starch and casein; humectants like gluconic acid and glycerin; vitamins such as $B_1$, $B_2$, $B_6$, $B_{12}$ and C; minerals, including water-soluble forms of calcium, magnesium, potassium, sulfur and zinc; and nicotine.

An adhesive according to the present invention is particularly well-suited for use with agents which exist only in water-solution. For example, chlorhexidine digluconate is a well-known broad-spectrum antimicrobial that only exists as a water-based compound, i.e., chlorhexidine digluconate cannot be dried down to a solid. Addition of chlorhexidine digluconate to a conventional, solvent-based adhesive, which is not water-miscible, would result in an emulsion.

The present invention also contemplates the production of a water-swellable adhesive that is suitable for use in wound dressings and other medical products, especially those that come into contact with bodily fluids. Thus, the uncured adhesive composition of the present invention can be spread or coated onto various backings, thereby to form dressings, drapes, tapes and the like, by means well-known to the industry, such as drawing, rolling and spraying. A preferred backing material in this context is a polyurethane film having a thickness of between about 0.0005 and 0.0015 inch (about 0.00013 to 0.0038 cm). The adhesive can be uniformly coated onto such film material to a wet thickness of about 001 to 0.003 inch (about 0.0025 to 0.007 cm) and dried at a temperature in the range of 60° C. The film carrying the dried adhesive layer thus obtained is then fully cured, e.g., by exposure to ultraviolet radiation, typically between 219 and 425 nanometers. A suitable exposure would be for about 20 seconds at 0.5 watts per square centimeter, but equivalent exposures are suitable. The result is a dressing with a fully cured, solvent-resistant, water swellable, transparent adhesive with a MVTR of about 6700 $g/m^2/24$ hours.

According to the present invention, a polymer adhesive as described above can be applied, preferably after the dissolution thereinto of at least one bioactive agent, to a flexible backing suitable for a wound dressing or drape, and then is subjected to low-temperature curing, i.e. by cross-linking irradiation. (Before the exposure to actinic radiation, the polymer adhesive is preferably subjected to low-temperature removal of any solvent which is present.) In this manner, the polymer adhesive is cured to form a single-phase solid retaining the hydrophilic nature of the prepolymer starting material. Alternatively, the polymer adhesive may be cured on a first substrate and subsequently laminated to a second substrate.

The examples which follow serve further to illustrate the present invention.

Example 1. Adhesive Formulation A

Isophorone diisocyanate was reacted with a glycerin-based triol which was adducted with ethylene oxide and propylene oxide (molecular weight: 10,000). The ethylene oxide was approximately 75 weight-percent of the adduct. The resulting capped prepolymer had an NCO-value of 2.8. Hydroxyethyl methacrylate (HEMA) was added to this capped prepolymer in an amount to react with 80% of the free NCOs and reacted for two hours under nitrogen at 35° C. One hundred grams of water were then added to 100 grams of the derivatized capped prepolymer. The reaction mixture was stirred for 60 minutes until an increase in viscosity was noted and some entrapment of carbon dioxide, generated by the reaction, occurred. Ethanol (200 grams) was added to reduce viscosity and the reaction mixture was then stirred for an additional twenty minutes at room temperature. Sufficient ammonium hydroxide was then added to halt chain extension, bringing the pH of the mixture to about 10. A photoinitiator, 2,2-diethoxyacetophenone, was added to a concentration of 1% of total composition weight. The resulting composition was stable, had low viscosity and was clear, with approximately 30% non-volatiles. Upon drying and curing by exposure to ultraviolet radiation, a fully cured pressure-sensitive adhesive which swelled in the presence of water was obtained.

Example 2. Adhesive Formulation B

To the capped prepolymer of Example 1 (NCO-value: 2.8), HEMA was added to react with 20% of the free NCO groups and reacted for two hours under nitrogen at 35° C. Water (100 grams) was then added to 100 grams of the derivatized capped prepolymer. The reaction mixture was stirred for fifteen minutes until an increase in viscosity was noted and there occurred some entrapment of carbon dioxide generated by the reaction. Two hundred grams of ethanol were added, and the reaction mixture was then stirred for an additional twenty minutes at room temperature. The reaction mixture was periodically tested for adhesiveness during this time by removing small samples, partially drying each sample, and touch-testing for "tack." Sufficient ammonium hydroxide was then added to halt chain extension, bringing the pH of the mixture to about 10. After this mixture was completely reacted, 2,2-diethoxyacetophenone was added to a concentration of 1% of the total composition weight. The resulting product was stable, had low viscosity, was clear with approximately 30% non-volatiles. Upon drying and U.V. curing, a fully cured pressure-sensitive adhesive which swelled in the presence of water was obtained.

Example 3. Wound Dressing

A uniform coating of the uncured wet polyurethane adhesive from Example 1 was applied to a 1.5 mil-thick (0.0015 inch or 0.0038 cm) polyurethane film on a polyethylene liner using a number 25 Mayer rod. The coating was then dried at 60° C. for ten minutes. After drying, the adhesive coated film was exposed to U.V. radiation at 425 nm for five minutes at 0.007 watts/cm$^2$. The adhesive exhibited excellent tack and swelled moderately in the presence of water.

Example 4. Wound Dressing

A uniform coating of the uncured wet polyurethane adhesive from Example 2 was applied, via a number 25 Mayer rod, to a 1.5 mil-thick polyurethane film on a polyethylene liner. The coating was then dried at 60° C. for ten minutes. After drying, the adhesive-coated film was exposed to U.V. radiation at 425 nm for five minutes at 0.007 watts/cm$^2$. The adhesive exhibited excellent tack and swelled greatly in the presence of water.

Example 5. Wound Dressing with Antimicrobial

Five grams of a 45% polyvinylpyrrolidoneiodine complex (PVP-I) was added to 100 ml of the uncured wet polyurethane adhesive formulation of Example A uniform coating of this polyurethane adhesive was applied to a 1.5 mil-thick polyurethane film on a polyethylene liner by means of a number 25 Mayer rod. The coating was then dried at 60° C. for sixty minutes. After drying, the adhesive coated film was exposed to U.V. radiation at 425 nm for five minutes at 0.007 watts/cm$^2$.

Example 6. Wound Dressing with Antimicrobial

Five grams of a 20% chlorhexidine digluconate water solution was added to 200 ml of the uncured wet polyurethane adhesive formulation of Example 1. With a number 25 Mayer rod, a uniform coating of this polyurethane adhesive was applied to a 1.5 mil-thick polyurethane film on a polyethylene liner. The coating was then dried at 60° C. for sixty minutes. After drying, the adhesive-coated film was exposed to U.V. radiation at 425 nm for five minutes at 0.007 watts/cm$^2$.

Example 7. Wound Dressing with Antimicrobial

Five grams of a 20% gentamicin water solution was added to 100 ml of the uncured wet polyurethane adhesive formulation of Example 1. A uniform coating of this polyurethane adhesive was applied to a 1.5 mil-thick polyurethane film on a polyethylene liner by means of a number 25 Mayer rod. The coating was then dried at 60° C. for sixty minutes. After drying, the adhesive-coated film was exposed to U.V. radiation at 425 nm for five minutes at 0.007 watts/cm$^2$.

Example 8 Wound Dressing with Coagulant

Five grams of a 20% thrombin water solution was added to 100 ml of the uncured wet polyurethane adhesive formulation of Example 1. A uniform coating of this polyurethane adhesive was applied to a 1.5 mil-thick polyurethane film on a polyethylene liner via a number 25 Mayer rod. The coating was then dried at 60° C. for sixty minutes. After drying, the adhesive-coated film was exposed to U.V. radiation at 425 nm for five minutes at 0.007 watts/cm$^2$.

Example 9. Wound Dressing with Protein

One-half gram of a 10% glucose oxidase water solution was added to 100 ml of the polyurethane adhesive formulation of Example 1. A uniform coating of this polyurethane adhesive was applied to a polyurethane film (1.5 mil) on a polyethylene liner by means of a number 25 Mayer rod. The coating was then dried at 60° C. for sixty minutes. After drying, the adhesive-coated film was exposed to U.V. radiation at 425 nm for five minutes at 0.007 watts/cm$^2$.

Example 10. Antimicrobial Activity

The biological activity of the dressing prepared according to Examples 6 and 7, respectively, was determined by a "Zone of Inhibition" test, whereby discs of dressing, 19 mm in diameter, were placed on agar (TSA) plates that had been inoculated with 0.5 McFalland standard of *Staphylococcuscus aureus* or *Escherichia coli*. After incubation for 18 hours at 37° C., the zones of inhibition of bacterial growth were measured and recorded. Control discs for comparison were made following the same procedures outlined in Examples 6 and 7 but using an acrylic-based adhesive composition ("MD-0129"; product of Semex Medical Corp.) or a rubber-based adhesive system ("Nacor 72-9574"; National Starch Corp.) in place of the polyurethane-based adhesive composition of the present invention. The results are shown below:

| Wound Dressing | S. aureus | E. coli |
| --- | --- | --- |
| Example 6 (chlorhexidine digluconate) | 4 mm | 4 mm |
| Example 7 (gentamicin) | 8 mm | 8 mm |
| Acrylic-based adhesive* (chlorhexidine digluconate) | 0 mm | 0 mm |
| Acrylic-based adhesive (gentamicin) | 0 mm | 0 mm |
| Rubber-based adhesive* (chlorhexidine digluconate) | 0 mm | 0 mm |
| Rubber-based adhesive (gentamicin) | 0 mm | 0 mm |

*Coagulation observed

Example 11. Moisture Vapor Transmission Rate

Ten milliliters of distilled water were contained in a vial having a 1.8 cm-diameter opening which was covered with a polyurethane adhesive film having a nominal thickness of 1 mil (0.001 inch or 0.0025 cm). The arrangement was weighed, at 36° C. (saturated humidity) for 24 hours and reweighed to determine water loss. Moisture vapor permeability rate, expressed in terms of "g/m$^2$/24 hours," was calculated. For comparison, a 1 mil-thick acrylic adhesive film ("TM1620-00"; product of Semex Medical Corp.) and a 1 mil-thick polyisobutylene rubber adhesive film ("ARclad"; product of Adhesive Research, Inc.) were tested in the same fashion. The results are as shown below:

| Film Type | MVTR |
| --- | --- |
| Polyurethane adhesive film | 6.686 |
| Acrylic adhesive film | 2.361 |
| Isobutylene rubber adhesive film | 1.715 |
| Open Vial (no film) | 10.229 |

Example 12. Water Absorption

The films from Example 11, including the comparison films, were soaked in water, patted dry with a paper towel, and weighed. The films were then dried in an oven for 1 hour at 60° C. and reweighed. The percentage of water absorption ("absorp. %") was calculated for each film by dividing the difference between the wet (soaked) weight and the dry weight by the dry weight. The results are as shown below:

| Film Type | Absorp. % |
| --- | --- |
| Polyurethane adhesive film | 397% |
| Acrylic adhesive film | 15.5% |
| Isobutylene rubber adhesive film | 0.2% |

What is claimed is:

1. An adhesive composition comprising a polymer adhesive that is soluble or dispersible in water and is low-temperature curable to form a solid which is single-phase at ambient temperature, pressure-sensitive, dermatologically acceptable, moisture vapor-permeable, and resistant to dissolution when exposed to water.

2. An adhesive composition as claimed in claim 1, wherein said adhesive, after curing, swells without dissolving when exposed to water.

3. An adhesive composition as claimed in claim 1, wherein said polymer adhesive is the product of a process comprising the step of subjecting a water-soluble derivatized capped prepolymer which comprises a plurality of first terminal groups and a plurality of low-temperature curable groups to chain extension in the presence of a chain extension agent reactive with said first terminal groups, whereby a polymer is formed, until said polymer attains a determined level of tackiness, when said chain extension is halted by addition of a chain termination agent reactive with said first terminal groups.

4. An adhesive composition as claimed in claim 3, wherein said derivatized capped prepolymer is reacted with an excess, based on the content of said first terminal group of said derivatized capped prepolymer, of said chain extension agent.

5. An adhesive composition as claimed in claim 3, wherein said first terminal group is an isocyanate group.

6. An adhesive composition as claimed in claim 5, wherein said chain extension agent is water, a polyol or a polyamine.

7. An adhesive composition as claimed in claim 3, wherein said first terminal group is an ester group.

8. An adhesive composition as claimed in claim 7, wherein said chain extension agent is ammonia or a polyamine.

9. An adhesive composition as claimed in claim 5, wherein said chain termination agent is ammonia.

10. An adhesive composition as claimed in claim 3, wherein said derivatized capped prepolymer is formed by reacting a water-soluble capped prepolymer comprising a plurality of said first terminal groups with a derivatizing agent comprising a first functional group which is reactive with said first terminal groups and a second functional group which is low-temperature curable, whereby a portion of said first terminal groups of said capped prepolymer are reacted with said first functional group of said derivatizing agent.

11. An adhesive composition as claimed in claim 10, wherein said second functional group is capable of low-temperature cure under the action of actinic radiation, pH shift or free radicals.

12. An adhesive composition as claimed in claim 11, wherein said second functional group is an ethylenically unsaturated group.

13. An adhesive composition as claimed in claim 10, wherein about 5 to 80% of said first terminal groups of said capped prepolymer are reacted with said first functional group of said derivatizing agent.

14. An adhesive composition as claimed in claim 13, wherein about 5 to 50% of said first terminal groups of said capped prepolymer are reacted with said first functional group of said derivatizing agent.

15. An adhesive composition as claimed in claim 10, wherein said first terminal group is an isocyanate group and said first functional group is a hydroxyl group or an amine group.

16. An adhesive composition as claimed in claim 15, wherein said derivatizing agent is a hydroxyalkyl acrylate, methacrylate, crotonate or itaconate.

17. An adhesive composition as claimed in claim 10, wherein said first terminal group is an ester group and said first functional group is an amine group.

18. An adhesive composition as claimed in claim 17, wherein said derivatizing agent is an aminoalkyl amide of a ($C_1$-$C_6$)-α,β-unsaturated carboxylic acid.

19. An adhesive composition as claimed in claim 3, wherein said derivatized capped prepolymer is formed by reacting a water-soluble prepolymer with one or more siloxane compounds comprising a low-temperature curable group.

20. An adhesive composition as claimed in claim 10, wherein said capped prepolymer is formed by reacting a water-soluble prepolymer comprising a plurality of a second terminal group which is reactive with said first terminal group, with a polyfunctional capping agent comprising a plurality of said first terminal group.

21. An adhesive composition as claimed in claim 20, wherein said first terminal group is an isocyanate group and said second terminal group is a hydroxyl group.

22. An adhesive composition as claimed in claim 21, wherein said prepolymer is a polyoxyalkylene polyol.

23. An adhesive composition as claimed in claim 20, wherein said first terminal group is an ester group and said second terminal group is an amine group.

24. An adhesive composition as claimed in claim 23, wherein said prepolymer is a polyaminoalkylene polyamine.

25. An adhesive composition as claimed in claim 20, wherein said prepolymer is formed by reacting a first water-soluble monomer comprising a plurality of said second terminal group with a second water-soluble monomer reactive with said second terminal group.

26. An adhesive composition as claimed in claim 25, wherein said second terminal group is a hydroxyl group.

27. An adhesive composition as claimed in claim 26, wherein said first water-soluble monomer is a polyol and said second water-soluble monomer is an epoxide compound.

28. An adhesive composition as claimed in claim 27, wherein said polyol is ethylene glycol, glycerol, trimethylolpropane or pentaerythritol.

29. An adhesive composition as claimed in claim 28, wherein said first water-soluble monomer is ethylene glycol, glycerol or a mixture of ethylene glycol and glycerol and said second water-soluble monomer is ethylene oxide.

30. An adhesive composition as claimed in claim 28, wherein said prepolymer has a molecular weight of about 3 to 15 kilodaltons.

31. An adhesive composition as claimed in claim 27, wherein said prepolymer is a copolymer which comprises at least 20% by weight of ethylene oxide moieties.

32. An adhesive composition as claimed in claim 25, wherein said second terminal group is an amine group.

33. An adhesive composition as claimed in claim 32, wherein said first water-soluble monomer is a polyamine and said second water-soluble monomer is an aziridene compound.

34. An adhesive composition as claimed in claim 20, wherein said prepolymer is a copolymer.

35. An adhesive composition as claimed in claim 34, wherein said copolymer comprises polyvinylpyrrolidone.

36. An adhesive composition as claimed in claim 1, wherein said polymer adhesive is the product of a process comprising the steps of i) reacting a compound comprising a plurality of hydroxyl groups and a polyisocyanate compound to form an isocyanate-terminated polyurethane capped prepolymer, ii) reacting a portion of the terminal isocyanate groups of said polyurethane capped prepolymer with a derivatizing agent comprising a group reactive with isocyanate and a low-temperature curable group to form a derivatized capped prepolymer, and iii) reacting said derivatized capped prepolymer with a chain extension agent reactive with isocyanate to effect chain extension of said derivatized capped prepolymer, whereby a polymer is formed, until said polymer attains a determined level of tackiness, wherein said chain extension is halted by addition of a chain termination agent reactive with isocyanate.

37. An adhesive composition as claimed in claim 1, further comprising a bioactive agent dissolved therein.

38. A adhesive composition as claimed in claim 37, wherein said bioactive agent is soluble in or miscible with water.

39. An adhesive composition as claimed in claim 37, wherein said bioactive agent is a protein, an enzyme, a growth factor, a hormone, a biocidal agent, an antiseptic agent, an antibacterial agent, an antifungal agent, an antiviral agent, an anti-histamine, an anti-inflammatory agent, an anti-pruritic agent, a keratolytic agent, an skin-protective agent, a rubefacient, a topical anesthetic, a hemostatic agent, an anti-anginal agent, a vitamin, a nutritional mineral, a water-soluble cellulose compound, collagen or nicotine.

40. A dermatologically-acceptable, moisture vapor-permeable, pressure-sensitive adhesive composition that is a single-phase solid at ambient temperature and resists dissolution when exposed to water, comprising a polymer adhesive which is the product of a process comprising the steps of i) providing a water-soluble derivatized capped prepolymer which comprises a first terminal group and a low-temperature curable group, ii) subjecting said water-soluble derivatized capped prepolymer to chain extension in the presence of a chain extension agent reactive with said first terminal group, whereby a polymer is formed, until said polymer attains a determined level of tackiness, when said chain extension is halted by addition of a chain termination agent reactive with said first terminal groups, and iii) subjecting said polymer to low-temperature curing.

41. An adhesive composition as claimed in claim 40, wherein in step iii, said low-temperature curing is effected by exposure to ultraviolet radiation or an electron beam.

42. An adhesive composition as claimed in claim 40, further comprising a bioactive agent dissolved therein.

43. An adhesive composition as claimed in soluble.

44. A water vapor-permeable, pressure-sensitive adhesive wound dressing, comprising a flexible backing coated with a pressure-sensitive adhesive layer provided on at least a portion of the surface of said backing, wherein said adhesive layer comprises an adhesive composition as claimed in claim 40.

45. A wound dressing as claimed in claim 44, wherein a bioactive agent is dissolved in said adhesive layer.

46. A wound dressing as claimed in claim 45, wherein said bioactive agent is water-soluble.

47. A wound dressing as claimed in claim 44, wherein said adhesive layer has moisture vapor permeability of about 6700 g/m$^2$/24 hours.

48. A wound dressing as claimed in claim 44, wherein said flexible backing is a polyurethane film.

49. A process for producing a water vapor-permeable, pressure-sensitive adhesive wound dressing which comprises the steps of
 i) providing a flexible backing,
 ii) applying to at least a portion of the surface of said backing an adhesive composition as claimed in claim 3, and
 iii) subjecting said adhesive composition to low-temperature cure.

50. A process for producing a polymer adhesive that is soluble or dispersible in water and is low-temperature curable to form a solid which is single-phase at ambient temperature, pressure-sensitive, dermatologically acceptable, moisture vapor-permeable, and resistant to dissolution when exposed to water, which comprises the steps of
 i) providing a derivatized capped prepolymer comprising a plurality of first terminal groups, and
 ii) reacting said derivatized capped prepolymer with a chain extension agent reactive with said first terminal groups to effect chain extension of said derivatized capped prepolymer, whereby a polymer is formed, until said polymer attains a determined level of tackiness, when said chain extension is halted by addition of a chain termination agent reactive with said first terminal groups.

51. A process for producing a polymer adhesive that is soluble or dispersible in water and is low-temperature curable to form a solid which is single-phase at ambient temperature, pressure-sensitive, dermatologically acceptable, moisture vapor-permeable, and resistant to dissolution when exposed to water, which comprises the steps of
 i) reacting a compound comprising a plurality of hydroxyl groups and a polyisocyanate compound to form an isocyanate-terminated polyurethane capped prepolymer,
 ii) reacting a portion of the terminal isocyanate groups of said polyurethane capped prepolymer with a derivatizing agent comprising a group reactive with isocyanate and a low-temperature curable group to form a derivatized capped prepolymer, and
 iii) reacting said derivatized capped prepolymer with a chain extension agent reactive with isocyanate to effect chain extension of said derivatized capped prepolymer, whereby a polymer is formed, until said polymer attains a determined level of tackiness, when said chain extension is halted by addition of a chain termination agent reactive with isocyanate.

52. A process for producing a dermatologically-acceptable, moisture vapor-permeable, pressure-sensitive adhesive composition that is a single-phase solid at ambient temperature and resists dissolution when exposed to water, which comprises the step of subjecting a polymer adhesive produced by a process as claimed in claim 50 to low-temperature cure.

53. A process for producing a dermatologically-acceptable, moisture vapor-permeable, pressure-sensitive adhesive composition that is a single-phase solid at ambient temperature and resists dissolution when exposed to water, which comprises the step of subjecting a polymer adhesive produced by a process as claimed in claim 51 to low-temperature cure.

* * * * *